(12) United States Patent
Smirthwaite et al.

(10) Patent No.: US 8,361,158 B2
(45) Date of Patent: Jan. 29, 2013

(54) CANINE PROSTHETIC ELBOW JOINT

(76) Inventors: Amie Diana Smirthwaite, Bath (GB); Paul Thomas Smirthwaite, Bath (GB)

( * ) Notice: Subject to any disclaimer, the term of this patent is extended or adjusted under 35 U.S.C. 154(b) by 318 days.

(21) Appl. No.: 12/526,348

(22) PCT Filed: Feb. 6, 2008

(86) PCT No.: PCT/GB2008/000421
§ 371 (c)(1),
(2), (4) Date: Nov. 3, 2009

(87) PCT Pub. No.: WO2008/096139
PCT Pub. Date: Aug. 14, 2008

(65) Prior Publication Data
US 2010/0145465 A1 Jun. 10, 2010

(30) Foreign Application Priority Data

Feb. 7, 2007 (GB) .................................. 0702380.7

(51) Int. Cl.
*A61F 2/38* (2006.01)
(52) U.S. Cl. .................. 623/20.11; 623/20.13
(58) Field of Classification Search ............... 623/18.11, 623/20.11–20.13, 23.39, 23.4, 23.41, 23.43
See application file for complete search history.

(56) References Cited

U.S. PATENT DOCUMENTS

| | | | | |
|---|---|---|---|---|
| 3,990,117 A * | 11/1976 | Pritchard et al. | ............ | 623/20.12 |
| 4,479,457 A | 10/1984 | Rotolo | | |
| 5,911,197 A | 6/1999 | Schmid | | |
| 6,162,253 A | 12/2000 | Conzemius et al. | | |
| 6,306,171 B1 | 10/2001 | Conzemius et al. | | |
| 7,419,507 B2 * | 9/2008 | Cook et al. | ................. | 623/20.13 |
| 2004/0220675 A1 | 11/2004 | Lewis et al. | | |
| 2005/0043806 A1 | 2/2005 | Cook et al. | | |
| 2007/0073408 A1 | 3/2007 | Acker et al. | | |
| 2007/0245583 A1 | 10/2007 | Tindall | | |
| 2008/0154384 A1 | 6/2008 | Acker et al. | | |
| 2009/0222012 A1 | 9/2009 | Karnes et al. | | |

* cited by examiner

*Primary Examiner* — David Isabella
*Assistant Examiner* — Suba Ganesan
(74) *Attorney, Agent, or Firm* — Stites & Harbison PLLC; Marvin Petry

(57) ABSTRACT

The application relates to a prosthetic canine elbow joint (1) comprising a radioulnar component (12) mountable in a trochlear notch of the ulna (2) and an articular fovea of a radius which is engagable with a humeral component (10) mountable on a trochlear bone portion of a humerus (4) to permit relative movement between the humerus (4) and ulna (2). The humeral component (10) is thus mounted e.g. hooked stably on a piece of bone extending between the medial and lateral condyles thereby making use of the intrinsic strength of bone. The humeral component (10) may include an opening (26) alignable with the supratrochlear foramen to receive the anconeal process (6) of the ulna (2) during articulation of the joint, thereby promoting freedom of movement.

7 Claims, 4 Drawing Sheets

CANINE PROSTHETIC ELBOW JOINT

TECHNICAL FIELD

This invention relates to replacement canine elbow joints.

BACKGROUND OF THE INVENTION

Various degenerative conditions, such as osteoarthritis and dysplasia, can affect the function of the elbow. Surgical treatment either to repair or replace the joint is necessary to avoid the joint becoming useless.

Replacement elbow joints for dogs have already been proposed.

US Patent Application Publication No. 2004-220675 discloses a prosthetic elbow joint for a dog in which a humeral component having an elongate stem and spiral grooved cylindrical head is engaged with a corresponding spiral ridge on an ulnar component that is attached to the ulna. This document suggests that the grooved and ridged nature of the replacement joint provides desirable lateral stability for the joint. The ulnar component is implanted by cutting an extensive L-shaped portion out of the ulna. To prepare and implant this component requires very invasive surgery, which may disrupt ligaments and require extensive soft tissue dissection. This can lead to undesirably long recovery times.

US Patent Application Publication No. 2005-043806 proposes a less invasive canine elbow replacement technique. Here, the humeral component comprises a stem that is insertable between the medial and lateral condyles of the humerus into the medullary canal. To permit this, a trochlear portion of bone between the medial and lateral condyles is cut out. To fix the humeral component in place, a transcondylar screw is located between the medial and lateral columns of the humerus. The ulnar component defines a U-shaped cavity for cooperating with the humeral component. This component is attached to the ulna by using a jig to cut a squared portion at the proximal end of the ulna, where it is fixed using a pin down the ulna's canal and an anconeal screw. This implanting process requires the anconeal process of the ulna to be removed.

SUMMARY OF THE INVENTION

Expressed generally, the present invention proposes a prosthetic canine elbow joint in which the existing joint is resurfaced and the underlying bone is preserved. A less invasive implantation process is also disclosed. The inventors have designed an implant which can preserve more existing bone than known devices, which can reduce the disruption of the natural joint and give an improved outcome.

A first aspect of the invention provides a prosthetic elbow joint for attaching to a humerus, a. radius and an ulna of a dog, the joint having a humeral component comprising a first articular element for mounting on a trochlear bone portion of the humerus which joins its medial condyle to its lateral condyle, and a radioulnar component comprising a second articular element for mounting in the trochlear notch of the ulna and articular fovea of the radius, wherein the first and second articular elements are engagable with each other in a manner which permits relative movement therebetween. Preferably, the radius and ulna are secured together, e.g. clamped using a screw, to prevent relative motion between the ulna and radius. The elbow joint thus formed is a true hinge. In contrast to known prosthetic elbow joints, a portion of bone in the trochlea position (i.e. travelling substantially perpendicular to the bone axis between the medial and lateral condyles) is preserved. By mounting the humeral component on this portion of bone, the prosthetic joint can make use of the intrinsic strength of the bone. The humeral component can therefore be smaller and lighter than known arrangements. The humeral component resurfaces the trochlea, thereby maintaining load transfer to the subchondral bone.

Preferably, the humeral component includes a stem that is insertable in the intramedullary canal of the humerus. The stem may be cemented in place. The stem can provide axial stability of the humeral component.

Preferably, the humeral component includes an opening arranged to align with the supratrochlear foramen when the humeral component is mounted on the humerus such that a passageway through the humerus is maintained. The canine humerus is naturally formed with a through hole in the form of the supratrochlear foramen. This hole receives the anconeal process of the ulna during articulation of a normal elbow joint. Thus, to preserve freedom of movement and to minimise the amount of bone removal, it is desirable to maintain this through hole in the prosthetic joint.

Known elbow joints have used the supratrochlear foramen as a convenient opening with which to remove completely the trochlear bone portion between the medial and lateral condyles thereby creating a space for a completely prosthetic trochlear portion which can be inserted into the intramedullary canal and fixed in place using e.g. a transcondylar screw.

The present invention avoids the need for a transcondylar screw because the humeral component is mounted on a trochlear bone portion that extends between the medial and lateral condyles. This provides two advantages. Firstly, a transcondylar screw is not required to secure the humeral component, which can make surgery less invasive. Secondly, the trochlear bone portion is integral with the medial and lateral condyles, so can provide a structurally stronger connection than a transcondylar screw.

The more compact and less invasive nature of the joint of the invention may make replacement of the joint a viable option if the interface between the humeral and radioulnar components wears. This may represent an advantage compared with conventional prosthetic joints.

Preferably, the first and second articular elements have curved outer surfaces which are mutually co-operable to permit relative rotation between them. Preferably, this rotation is about a stable axis which constrains the relative movement of the humerus and ulna within a predetermined plane. For example, the articular elements may include co-operable cylindrical surfaces. The first articular element may have a convex outer surface, and the second articular element may have a concave outer surface adapted to receive the convex outer surface. Preferably, a bearing is provided between the curved outer surfaces of the first and second articular elements so that relative movement is smooth.

Preferably, the humeral component includes a hook adapted to grip the trochlear bone portion. The trochlear bone portion may be prepared (e.g. shaped using a cutting tool) to conform with the shape of the hook. For example, the hook may define a rectangular (box-like) opening. The trochlear bone portion may be squared off using a cutting tool before the humeral component is mounted thereon. The humeral portion may be cemented to the trochlear bone portion. The first articular element may be formed on an opposite surface of the humeral component from the hook. In this manner, the first articular element may mimic the trochlea it replaces. In other words, part of the trochlea may be cut away in preparing the trochlear bone portion for the hook of the humeral component such that, when the humeral component is in place, the first articular element provides a curved surface at a position corresponding to the replaced trochlea.

Preferably, the radioulnar component has a curved fixing surface arranged to contact the radius and ulna within the trochlear notch of the ulna and the articular fovea of the radial head. The trochlear notch and articular fovea are curved portions of bone that engage the trochlea in a normal elbow joint. The present invention aims to preserve the curvature of bone in this region of the radius and ulna in the prosthetic joint. There are two advantages to this. Firstly, preserving the curvature of the bone can permit less bone to be removed. Secondly, the curvature of bone can provide greater structural support for the second articular element (on the radioulnar component). Known prosthetic elbow joints propose radical reconfiguration of the proximal end of the ulna. Often, the anconeal process is completely removed and the trochlear notch reshaped as an L-shaped ledge. This requires an invasive process which may compromise clinical outcome.

Preferably, the radioulnar component includes a plurality of bone screws for attaching its curved fixing surface within the trochlear notch and articular fovea. The trochlear notch and articular fovea may be prepared to receive the radioulnar component. For example, the second articular surface on the ulnar component may be arranged to take the place of the natural surface of the trochlear notch and articular fovea. Thus, the trochlear notch and articular fovea may be deepened, i.e. a curved layer of bone may be removed, to receive the curved fixing surface of the radioulnar component such that the curved surface of the second articular element lies substantially in the position of the natural trochlear notch and articular fovea.

The radioulnar component may therefore comprise a curved plate having the second articular element formed on a concave inner surface and the curved fixing surface on the convex outer surface.

The humeral and radioulnar components discussed above may be independent aspects of the invention.

BRIEF DESCRIPTION OF THE DRAWINGS

An embodiment of the invention is now described with reference to the accompanying drawings, in which.

DETAILED DESCRIPTION; FURTHER OPTIONS AND PREFERENCES

Figure 1:
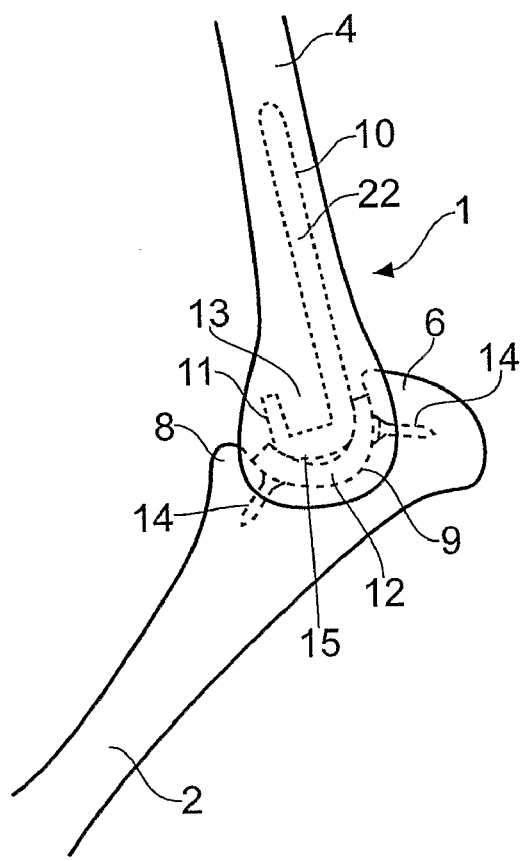
FIG. 1 shows a side view of a canine elbow joint having a prosthetic implant that is an embodiment of the invention.

In addition to the prosthetic canine elbow joint of the invention, the discussion below describes apparatus for preparing a distal end of a humerus to receive the humeral component of a prosthetic elbow joint, the apparatus including a reamer shaft that is insertable into the medullary canal of the humerus, and jig that is securably mountable on the shaft at the distal end of the humerus, wherein the jig is configured to guide a cutting tool to cut a trochlear bone portion of the humerus which joins its medial condyle to its lateral condyle into a predetermined shape suitable for receiving the humeral component. The reamer shaft can be adapted to clear a passageway in the medullary canal of the humerus. When the reamer is subsequently removed, this passageway may be used by a stem on the humeral component. The apparatus can include a cross handle that is reversibly attachable to the reamer shaft. The cross handle can be used to rotate the reamer shaft to clear the passageway.

The reamer shaft can define an axis substantially along the humerus. By fixing the jig with respect to this axis, the trochlear bone portion can be shaped in a way that causes the humeral component to adopt a predetermined orientation with respect to the humerus. Preparation of the humerus in this way can therefore be used to control the location and direction of relative movement within the prosthetic joint.

The jig may include a plurality of guide slots for orienting a cutting blade, the guide slots being arranged to permit movement of the cutting blade along the surfaces of the predetermined shape. For example, the plurality of guide slots may include:

an upper plane slot and a lower plane slot which are spaced apart and each extend substantially in a plane parallel to both a transcondyle direction and the direction of the reamer shaft;

a pair of side plane slots that are spaced apart from each other and extend substantially parallel from each other in a plane normal to the transcondyle direction; and a distal plane slot that extends substantially normal to the direction of the reamer shaft, whereby the predetermined shape of the bone after cutting is cuboidal. The planes defined by the upper plane slot and lower plane slot may diverge slightly, i.e. to give the shape of bone after cutting a trapezoidal cross-section. The corresponding internal faces of the hook converge in a similar manner to achieve a wedge-like fit between the bone portion and the hook.

As explained above, the humeral component may include a hook that is adapted to grip the prepared trochlear bone portion. By creating a cuboidal (i.e. squared-off edged) bone portion to fit snugly in a corresponding recess (hook) in the humeral component, the orientation of the humeral component with respect to the humerus can be more accurately controlled. Previous arrangements rely on the skill and eye of the surgeon for alignment accuracy.

The apparatus contrasts with known jigs for preparing a canine humerus. The known jigs are arranged to remove a transcondyle portion of bone located at the distal end of the supratrochlear foramen.

Also discussed below is apparatus for preparing a proximal end of a radius and an ulna to receive the radioulnar component of a prosthetic elbow joint, the apparatus including a cutting tool having a curved cutting edge arranged to cut an arc in bone when the cutting tool is moved in a cutting direction, and an elongate guide element for resting on the trochlear notch of the ulna, the guide element being attached to the cutting tool and protruding therefrom in the cutting direction. The apparatus is therefore adapted to deepen the trochlear notch and articular fovea by removing a curved portion of bone therefrom.

The cutting edge is arranged to oscillate along this curve to effect cutting. The cutting tool may oscillate about a rotation axis. The rotation axis may be along the same direction as the cutting direction.

The curved edge may lie on a circle. Preferably, the centre of the circle is defined by the elongate guide element. This can allow the curvature of the arc that is cut in the bone by the apparatus to be related to the position of the original trochlear notch.

Thus, the cutting tool may comprise a cutting blade in the form of a partial cylindrical sleeve having a U-shaped cross-section, the curved cutting edge being at one end of the sleeve and a driving element being attached to the other end of the sleeve, the driving element being drivable to effect oscillation of the cutting edge. The driving element may be an engagement bit (key) that is receivable in the chuck of an oscillating power tool. The guide element may be a rod. The cutting edge may be movable relative to the guide element to effect cutting. The guide element may be removable. Guide elements having different diameters may be used to enable the cutting tool to cut arcs of differing depths.

Also briefly discussed below are methods of implanting the humeral and radioulnar components of a prosthetic canine elbow joint. For example, a method of implanting a humeral component of a prosthetic canine elbow joint at a distal end of a humerus may include: inserting a reamer shaft into the medullary canal of the humerus; securely mounting a jig on the reamer shaft at the proximal end of the humerus; guiding a cutting tool with the jig to cut a region of bone between the medial and lateral condyles of the humerus to form a trochlear bone portion having a predetermined shape; removing the jig and reamer shaft; and mounting the humeral component on the trochlear bone portion of the humerus. Mounting the humeral component may include inserting a stem of the humeral component into the medullary canal. To create the trochlear bone portion having a predetermined shape, the method may include moving a cutting edge through: an upper plane and a lower plane which are spaced apart and extend in planes substantially parallel to both a transcondyle direction and the direction of the reamer shaft; a pair of side planes that are spaced apart from each other and extend substantially parallel with each other in a plane normal to the transcondyle direction; and a distal plane that extends substantially normal to the direction of the reamer shaft, whereby the predetermined shape of the trochlear bone portion is cuboidal. Furthermore, a method of implanting a radioulnar component of a prosthetic canine elbow joint on a proximal end of an ulna and a radius may include: moving a curved cutting edge in a medial-lateral direction through the radius and ulna underneath the trochlear notch to remove a layer of bone from the trochlear notch and articular fovea to thereby create a larger arcuate groove; and mounting the radioulnar component in the arcuate groove. Preferably, the method includes moving the curved cutting edge in a cutting direction defined by an elongate guide element which lies across the surface of the trochlear notch.

Turning now to the drawings, FIG. 1 shows a canine elbow joint comprising an articulated ulna 2 and humerus 4. The articulation is provided by a prosthetic elbow joint 1 shown in phantom. The elbow joint 1 is an embodiment of the invention.

The elbow joint 1 comprises a humeral component 10 that is attached to the humerus 4 and a radioulnar component 12 attached to the radius and ulna 2 using bone screws 14. The humeral component 10 and radioulnar component 12 engage one another in a way which permits relative movement between the humerus 4 and ulna 2. The radioulnar component 12 defines a concave cylindrical surface which receives a corresponding cylindrical drum on a distal end of the humeral component 10. The drum defines an axis about which the humeral and radioulnar components and therefore the humerus and ulna can rotate. A cylindrical shape is used to constrain the plane of rotation to prevent damage to elbow joint ligaments when the implant is in place.

The drum is retained in the cylindrical surface. A bearing (not shown), such as a layer of polyethylene is provided between the relatively movable surface to permit free and smooth movement.

For stability and strength, the humeral component 10 has a stem 22 which is cemented into a cavity reamed into the intramedullary canal of the humerus 4.

FIG. 1 shows the mounting position of the radioulnar component 12. This component has an outer curved surface which contacts a curved bone surface 9 within the trochlear notch of the ulna 2 and the articular fovea of the radial head. The ulna 2 and radius naturally present a curved cavity (the trochlear notch) in this region. The present invention preserves the curved nature of this area of bone. In practice, and as discussed below, the trochlear notch is deepened using a curved cutting tool to create the curved bone surface 9, whose curvature is matched to the curvature of the back surface of the ulnar component 12. The medial and lateral coronoid process 8, the anconeal process 6 and the radial head may all be preserved in the present invention. This permits a less invasive technique than conventional processes, which remove one or all of these bone portions.

FIG. 1 also shows that the cross-section at the distal end of the humeral component 10 is a hook 11 with a squared-off inside portion 13 and a curved outside portion 15 which forms the cylindrical drum. The hook 11 is attached to a portion of bone that extends naturally between the medial and lateral condyles of the humerus 4. The humeral component 10 therefore makes use of the natural strength of bone at the distal end of the humerus for its stability.

Figure 2:
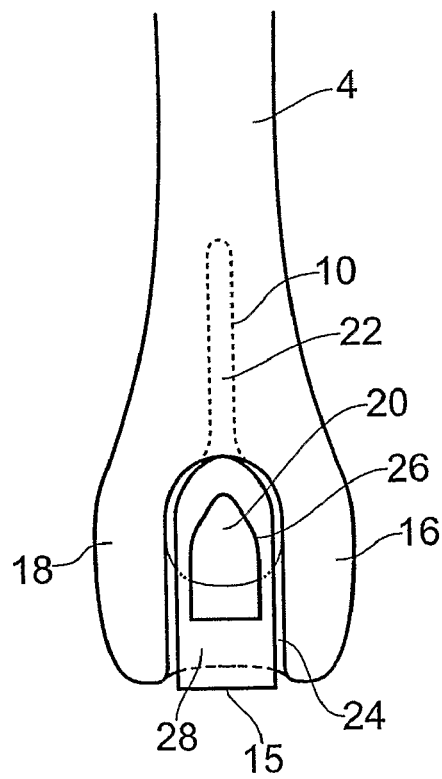
FIG. 2 shows a back view of the distal end of a canine humerus having the humeral component of the prosthetic implant attached thereto.

FIG. 2 shows a back view of the distal end of the humerus 4 with the humeral component 10 in place. The distal end of the humerus 4 has a medial condyle 16 and a lateral condyle 18 connected by a trochlear bone portion 24. A natural humerus has a trochlea in the trochlear bone portion. The trochlea engages the trochlear notch to provide the natural elbow joint. In the present invention, the trochlea is surgically prepared to form the trochlear bone portion 24 to be suitable to receive closely the hook 11 of the humeral component 10. This process is described below.

The canine humerus typically includes a supratrochlear foramen 20 extending through the humerus 4. The supratrochlear foramen 20 provides space for the anconeal process 6 of the ulna 2 during articulation of the joint. To provide freedom of movement of the prosthetic joint of the invention, it is therefore desirable to maintain this space. The body 28 of the humeral component 10 therefore has an opening 26 arranged to lie over the supratrochlear foramen 20 when implanted and sized to permit the anconeal process 6 of the ulna to pass therethrough during articulation of the joint.

Conventional elbow replacement procedures remove the trochlear bone portion 24 completely. The present invention preserves it, thereby incorporating some of the natural strength of bone into the replacement joint. This can also make the joint lighter as less material (e.g. metal) is needed for the joint components.

Figure 3:
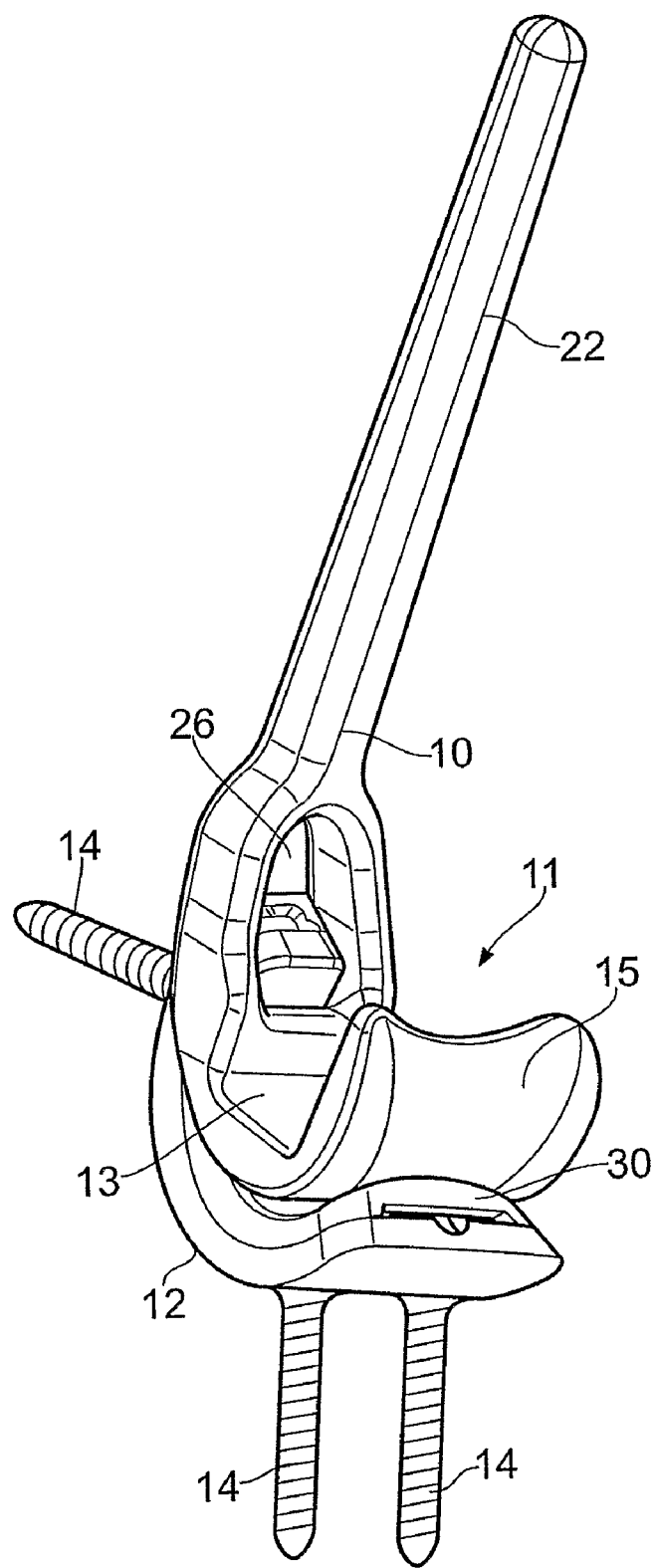
FIG. 3 shows a prosthetic canine elbow joint that is an embodiment of the invention.

FIG. 3 shows a perspective view of the humeral component 10 and the radioulnar component 12 in an engaged configuration in isolation. In this drawing, a bearing 30 comprising a layer of low friction plastic material is provided between the inner surface of the radioulnar component 12 and the curved outside portion 15 of the humeral component 10. In this embodiment, the curved outside portion 15 is bowed into a circumferential groove to create a saddle-like surface on the drum.

The bearing 30 has a corresponding central hump. This arrangement increases the lateral integrity of the joint by providing self-centring engagement between the components.

The opening 26 in the humeral component 10 also permits the tip of the radioulnar component 12 to pass therethrough, thereby enabling an extended range of motion between the ulna and humerus when in use.

In general, the prosthetic joint of the invention conserves more bone than conventional replacement joints. An advantage of this is that artificial ligaments need not be used. The natural ligaments can remain because the bone portions to which they are attached are conserved. For example, the lateral collateral ligament may be preserved.

Figure 4:
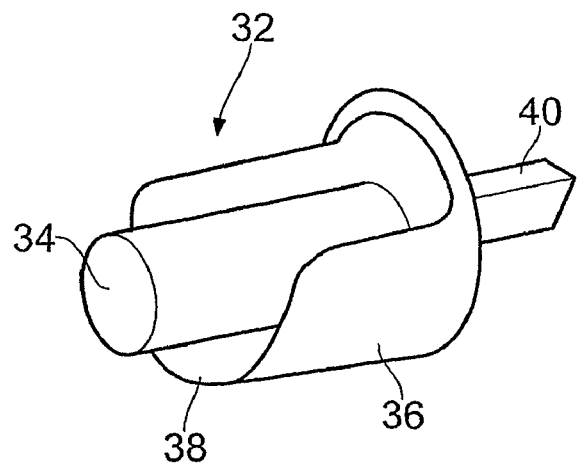
FIG. 4 shows a ulnar cutting tool for preparing an ulna for the implant of FIG. 3.

FIG. 4 shows a radioulnar cutting tool 32 which is used to prepare a radius and ulna 2 for receiving the radioulnar component 12. The cutting tool 32 has a guide pin 34 and a cutting sleeve 36 located coaxially therewith. In this example, the cutting sleeve 36 only surrounds about half of the circumference of the guide pin 34. A front end of the guide pin 34 protrudes beyond the front facing edge 38 of the cutting sleeve 36. A back end of the guide pin 34 is removably attached to the cutting sleeve 36. An elongate key member 40 is rigidly attached to the back end of the cutting sleeve 36 and protrudes therefrom to be receivable in the chuck of an oscillating tool (not shown). The oscillating tool can drive the cutting sleeve and cause it to oscillate about an axis defined by the key member 40. This axis is aligned with (preferably coincident with) the axis of the guide pin 34. The front facing edge 38 is serrated (e.g. has cutting saw teeth projecting therefrom). In use, the protruding end of the guide pin rests on the trochlear notch of the ulna. The cutting sleeve 36 oscillates about the guide pin axis. The tool is positioned so that the guide pin axis is in a medial-lateral direction. Pushing the tool along this direction causes a curved section to be cut out of the ulna (and radius) to permit the ulnar component to be received. The depth of cut depends on the diameter of the guide pin 34. A guide pin having a suitable diameter for the particular joint can be chosen and attached to the cutting sleeve before the cutting operation commences.

Figure 5:
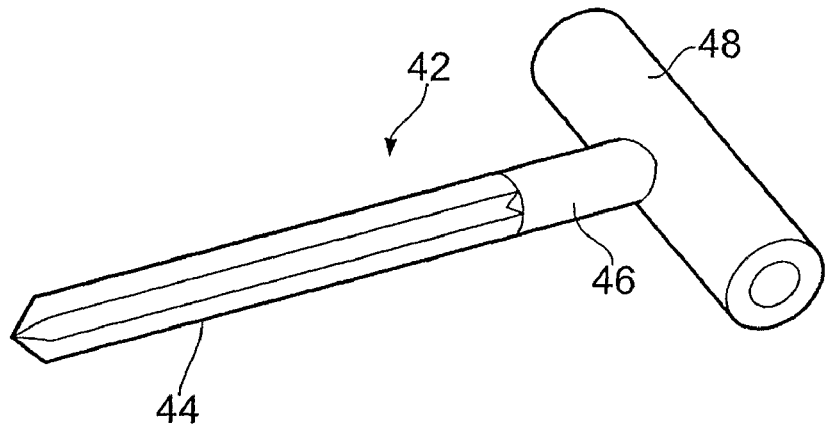
FIG. 5 shows a reamer with a detachable cross-bar.

FIG. 5 shows a reamer 42 for reaming the medullary canal of a humerus. It has a conventionally bladed reaming tip 44 at one end of an elongate body 46. A cross-bar 48 is attached to the other end of the elongate body 46. The cross-bar 48 is removable to permit other components to be mounted on the body 46. When inserted into the intramedullary canal, the elongate body 46 conveniently defines a stable axis along the humerus. This axis can be used to align further cutting operations, which prevents over-reliance on the eye of the surgeon.

Figures 6, 7:
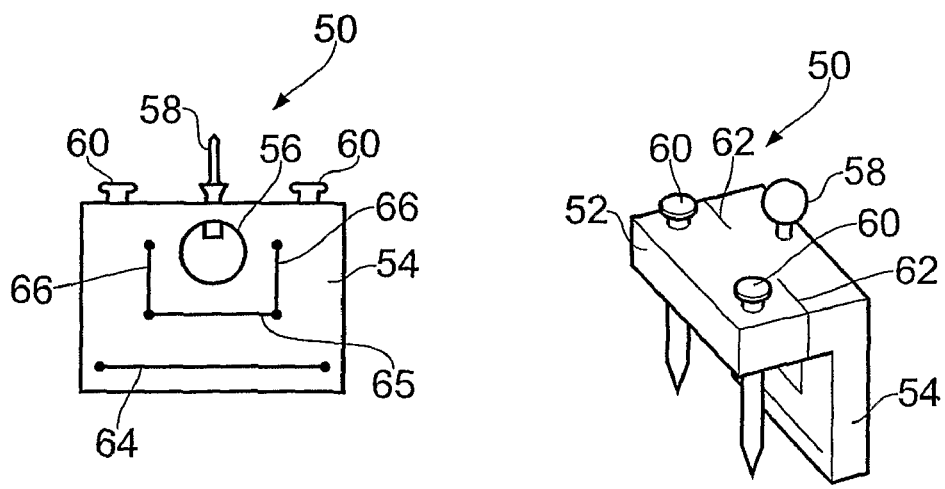
FIG. 6 shows a perspective view of a humeral cutting jig for preparing a humerus for the implant of FIG. 3.
FIG. 7 shows a back view of the humeral cutting jig of FIG. 6.

FIGS. 6 and 7 shows a cutting jig 50 for preparing the distal end of a humerus for the humeral component of a prosthetic elbow joint. The jig 50 comprises an L-shaped block with a top plate 52 and a back plate 54. The back plate 54 is adapted to be mounted on the elongate body 46 of the reamer 42. For this purpose the back plate 54 has a through hole 56 for receiving the reamer body 46. A thumbscrew 58 projects into the through hole 56 through the top plate 52 to clamp the jig 50 and fix it relative to the axis defined by the reamer body 46. To further secure the jig 50, two bone pins 60 pass through the top plate 52. These pins are secured to the distal end of the humerus to fix the jig's position.

The purpose of the jig 50 is as a guide for shaping the trochlear bone portion of the humerus to receive the hook of the humeral component. As shown above, the hook defines a squared-off recess. The jig 50 is therefore arranged to guide a cutting tool (not shown) to shape the trochlear bone portion into a corresponding block-like (e.g. cuboidal) shape. The jig 50 therefore comprises various slots to constrain the cutting plane of a cutting tool.

The top plate 52 has a pair of slots 62 through it. These slots are coplanar and lie in a plane that is substantially normal to the bone axis (reamer body 46) direction. A cutting blade moving in this plane would flatten the distal facing end of the humerus.

The back plate 54 has a pair of transverse slots 64, 65 and a pair of upright slots 66. The transverse slots 64, 65 are substantially parallel with each other and lie in transverse planes that are substantially parallel to both the bone axis direction and a transcondylar direction (i.e. a direction between equivalent points on the medial and lateral condyles). A cutting blade moving in these planes would cut the faces of the squared-off trochlear bone portion that contact the top and bottom surfaces of the hook in the humeral component.

The lower transverse slot 64 is wide enough to flatten the lower part of the distal end of the humerus. This can be achieved because the lower part of the humerus naturally curves upwards as it extends away from the distal end. This is not the case for the upper part. The upright slots 66 are therefore provided at each end of the upper transverse slot 65 to permit the layer of bone located above the upper transverse cut to be removed. The upright slots 66 lie in parallel planes that are normal to the transverse planes and parallel to the bone axis direction. A cutting blade moving in these planes would cut parallel to the axis of the humerus to form side walls for the trochlear bone portion. Referring to FIG. 2, the top part of the trochlear bone portion falls downward into the supratrochlear foramen. Thus, this provides a natural point at which the cut will complete to free a top cut-off portion of bone. Where there is no supratrochlear foramen, the top plate may contain a further pair of slots towards its proximal end.

Figure 8:
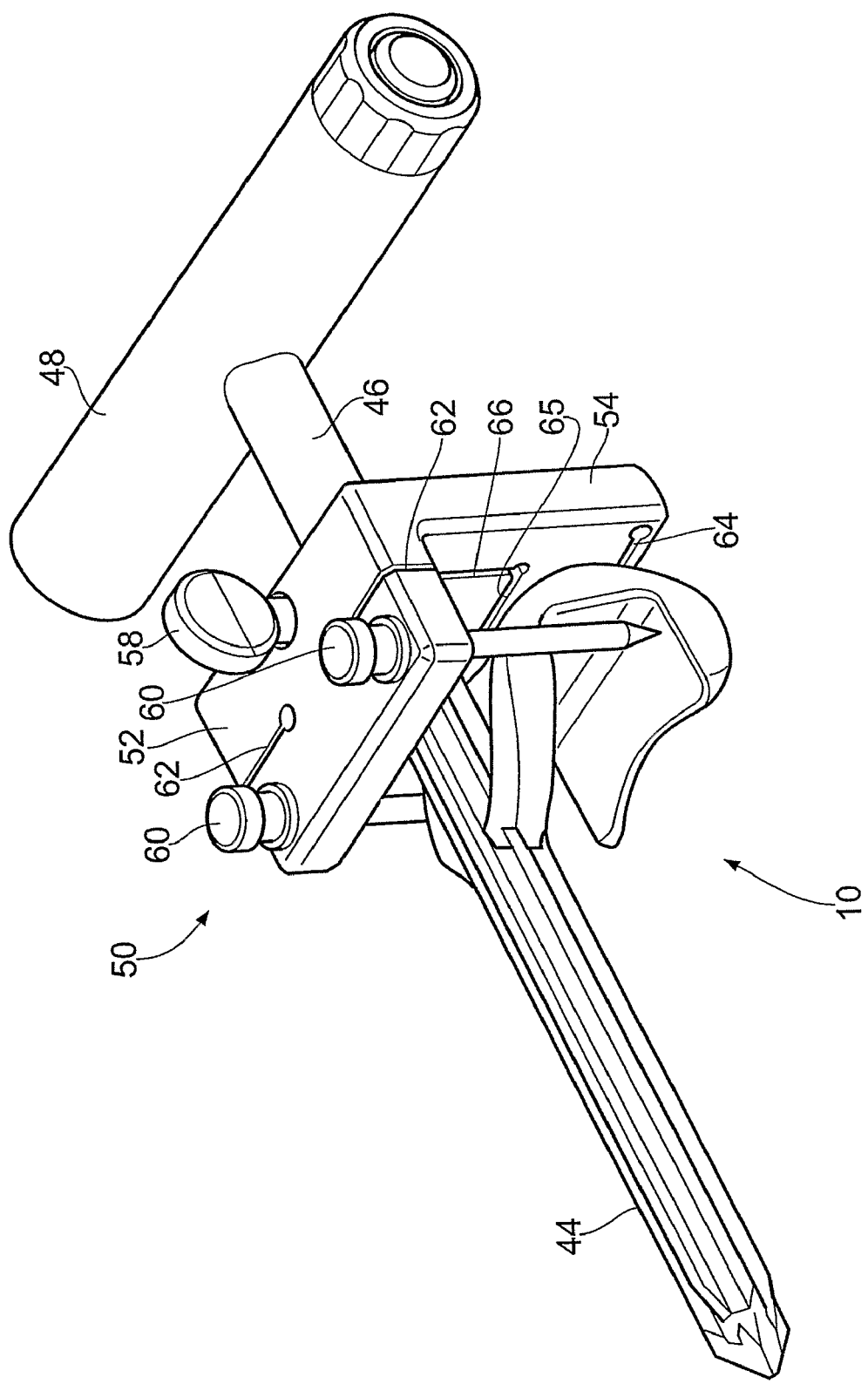
FIG. 8 shows a perspective view of the humeral cutting jig mounted on the reamer shaft with the humeral component superimposed to indicate the relative sizes of the apparatus

FIG. 8 shows the jig 50 mounted on the reamer body 46. To illustrate the planes that are cut by the various slots, the humeral component is superimposed.

To prepare the humerus, the surgeon first osteotimises the lateral epicondyle of the humerus and removes the tip of the anconeal process. The joint can then be dislocated to allow the reamer to be inserted and advanced into the intramedullary canal. After reaming, the cross-bar is removed and the jig is slid onto the reamer body until it touches the bone. The jig is then secured by tightening the thumbscrew and inserting the bone pins into bone.

After securing the jig, an oscillating saw blade is inserted through the guide slots to cut the bone. After cutting, the jig and reamer are removed, leaving a prepared surface to which the humeral component can be fixed, e.g. using cement or other suitable adhesive.

The invention claimed is:

1. A prosthetic elbow joint for attaching to a humerus and an ulna of a dog, the joint having:
   a humeral component comprising a first articular element mountable on a trochlear bone portion of the humerus, which portion extends between and joins together the humeral medial condyle and a humeral lateral condyle, and defines the supratrochlear foramen above it, wherein the humeral component includes an opening arranged to align with the supratrochlear foramen when the humeral component is mounted on the humerus such that a passageway through the humerus is maintained
   the first articular element including a stem which is insertable into the humerus, a curved portion connected to the stem and a hook extending up from the side of the curved portion opposite from the stem, and an ulnar component comprising a second articular element which is mountable in a trochlear notch of the ulnar element and which engages and moves relative to the curved portion of the first articular element.

2. An elbow joint according to claim 1, wherein the stem is insertable into an intramedullary canal of the humerus.

3. An elbow joint according to claim 1, wherein the first articular element and the second articular element are mutually co-operable to permit relative rotation between them.

4. An elbow joint according to claim 3, wherein the first articular element has a convex outer surface and the second articular element has a concave outer surface adapted to receive the convex outer surface.

5. An elbow joint according to claim 3 including a bearing between the curved outer surfaces of the first and second articular elements.

6. An elbow joint according to claim 1, wherein the ulnar component has a curved fixing surface arranged to contact the ulna within the trochlear notch.

7. An elbow joint according to claim 1, wherein the ulnar component includes a plurality of bone screws constructed to attach the curved fixing surface within the trochlear notch.

* * * * *